United States Patent [19]
Stevens et al.

[11] Patent Number: 5,990,350
[45] Date of Patent: Nov. 23, 1999

[54] PROCESS FOR MAKING GRANULAR L-LYSINE

[75] Inventors: Joseph Michael Stevens, Monticello; Thomas P. Binder, Decatur, both of Ill.

[73] Assignee: Archer Midland Company, Decatur, Ill.

[21] Appl. No.: 08/991,145

[22] Filed: Dec. 16, 1997

[51] Int. Cl.$^6$ .......................... C07C 229/00; C12P 13/08
[52] U.S. Cl. .......................... 562/562; 435/115; 424/438; 424/489; 426/2; 426/53
[58] Field of Search .................... 424/438, 489; 426/2, 53; 435/115; 562/562

[56] References Cited

U.S. PATENT DOCUMENTS

| | | | |
|---|---|---|---|
| 3,089,824 | 5/1963 | Wurster | 167/82 |
| 4,181,708 | 1/1980 | Dannelly | 424/482 |
| 4,327,118 | 4/1982 | Georgen et al. | 426/656 |
| 4,996,067 | 2/1991 | Kobayashi et al. | 426/96 |
| 5,133,976 | 7/1992 | Rouy | 426/72 |
| 5,300,318 | 4/1994 | Pierre et al. | 427/212 |
| 5,622,710 | 4/1997 | Binder et al. | 424/438 |

FOREIGN PATENT DOCUMENTS

| | | |
|---|---|---|
| 91460051.5 | of 0000 | European Pat. Off. . |
| WO 95/23129 | of 0000 | WIPO . |

OTHER PUBLICATIONS

Saksaoka et al, Coated feed activities for ruminants, CA: 110: 170254b, Dec. 1988.

*Primary Examiner*—Gary Geist
*Assistant Examiner*—Taylor Victor Oh
*Attorney, Agent, or Firm*—J.Warren Whitesel Laff, Whitesel & Saret, Ltd.

[57] ABSTRACT

Process for the efficient production of a substantially dust-free, free flowing granular L-Lysine in which the L-Lysine content is adjustable. Cells are removed from a fermentation broth containing L-Lysine to make a substantially cell free L-Lysine broth. Water is removed from the L-Lysine broth to form a concentrated L-Lysine broth. The L-Lysine content of the concentrated L-Lysine broth may be adjusted to be between about 35% and 76%, measured as a percent of freebase per kg, by adding material containing L-Lysine to provide an enriched L-Lysine broth. The enriched L-Lysine broth is agglomerated by means of an atomized spray of the enriched L-Lysine broth directed onto a fluidized bed of percolating L-Lysine particles. The L-Lysine particulates act as seeds for the agglomeration process wherein the L-Lysine particulates grow in size to provide a substantially dust-free, free flowing granular L-Lysine. Granules in the size range between about 177 micron and 1190 micron, and preferably between about 177 micron and 420 micron, are selected by means of a sieving process and bagged. Granules which are larger than about 1190 micron are ground down and combined with particles which are less than about 177 micron and recycled back to the fluidized bed to act as seeds in order to sustain the agglomeration process.

27 Claims, 1 Drawing Sheet

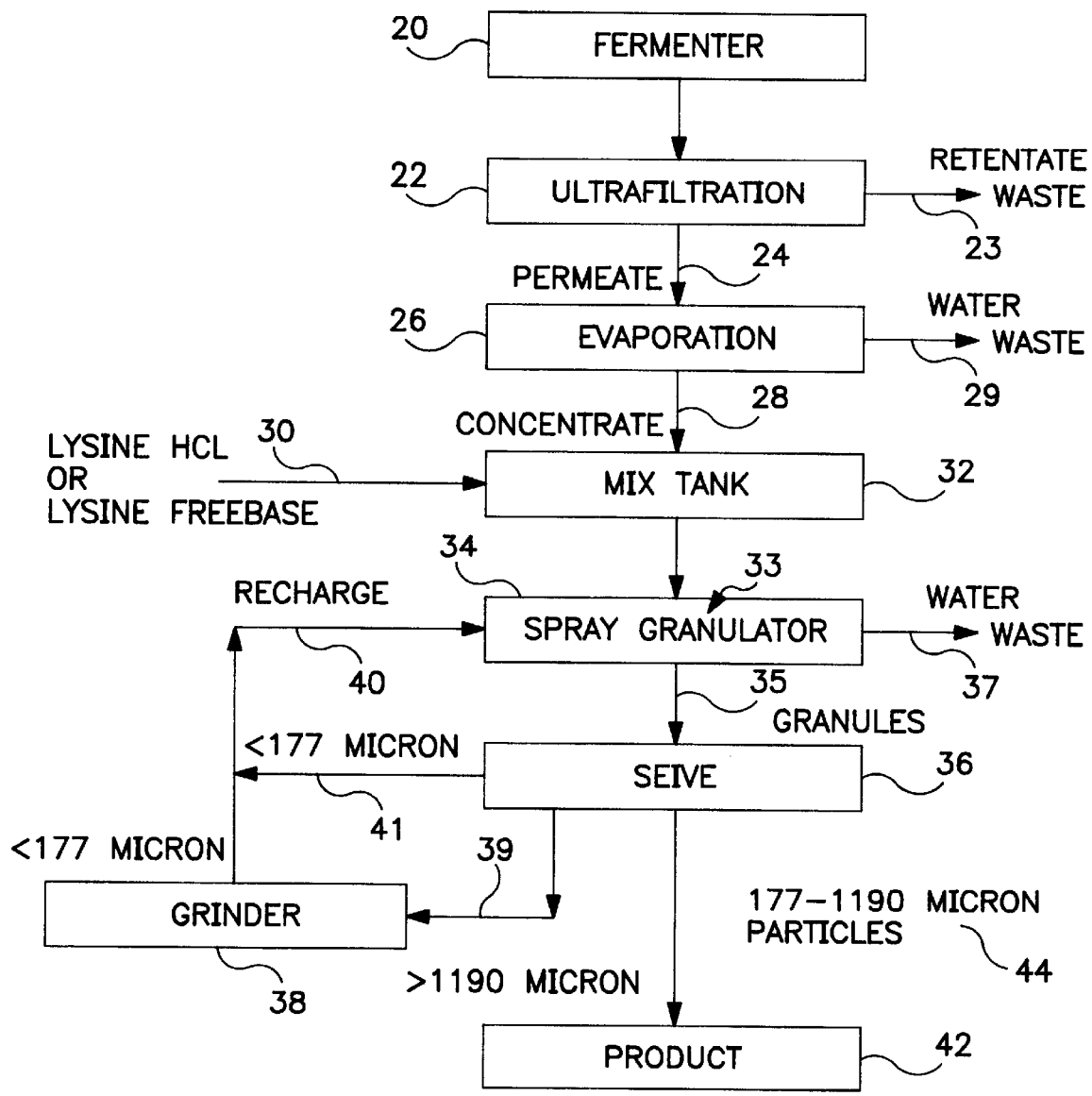

PROCESS FOR MAKING GRANULAR L-LYSINE

This invention relates to processes for producing granular L-Lysine from fermentation broth, and more particularly, to an accomplishment of the production of a granular L-Lysine product in which the L-Lysine content is adjustable without requiring extensive ion exchange.

BACKGROUND OF THE INVENTION

Lysine is an amino acid used extensively in the animal feed industry. The major form of L-Lysine used in the feed industry is L-LysineHCl (L-Lysine monohydrochloride). For many years, an L-LysineHCl solid has been produced by a process of fermentation, purification, crystallization and drying. After fermentation, the resulting broth may be rendered cell free by filtration or centrifugation. After filtration, the L-Lysine may be recovered from the fermentation broth by an ion exchange, which produces a liquid which is substantially L-Lysine free base. This solution may then be concentrated by evaporation.

Hydrochloric acid is usually added to the concentrated L-Lysine free base to form L-LysineHCl. This concentrated L-LysineHCl solution is crystallized to produce a product in the form of L-LysineHCl dihydrate (L-LysineHCl:$2H_2O$). This crystallized solid is thereafter dried to have less than one percent moisture.

This conventional product may have shortcomings. For example, it is dusty. During the handling of the product, the dust results in a loss of valuable material and sometimes causes an incomplete formulation. Also, human working conditions are made less healthful and more difficult by the dust contributed by the L-LysineHCl. Sometimes the product develops lumps during storage which are difficult to break up at the time of end use. In addition, the extensive use of ion exchange makes this process expensive. In particular, there is a need for a more economical process which avoids extensive ion exchange.

Direct spray drying of L-Lysine containing fermentation broth would avoid the extensive purification steps associated with the L-Lysine hydrochloride process, in particular the use of an expensive ion-exchange. However, consistent L-Lysine concentration in the final dry product would be difficult to achieve because the L-Lysine concentration in fermentation broth can vary considerably. Also, the product would b e dusty and difficult to use.

U.S. Pat. No. 5,431,933 describes a process for the production of an amino acid feed supplement which "still contains most of the solids content of the fermentation broth." The production of a fermentation broth at the industrial scale with 40 to 50 percent L-Lysine content is very difficult to achieve from an operational standpoint. Anyone skilled in the fermentation art is aware that upsets—contamination, power outages, operator error—are quite common and would likely produce material that was less than 40 to 50 percent L-Lysine and therefore unusable. This difficulty is compounded by the impurities associated with the media components, many of which are unrefined and vary in solids content and nutrient value from lot to lot. To avoid variance in media, fermentation would be constrained to specific and expensive media. These increases in operational input necessary to make a 40 to 50 percent L-Lysine product would cause the manufacturing costs to be prohibitive. In addition, the broth is dried to produce a powder. Powder is difficult to handle and can have detrimental health effects on workers due to dust inhalation. Thus, there is a need for an inexpensive process for the manufacture of a non-dusty L-Lysine product for use in feed supplements.

A process in which a non-dusty granular animal feed product is formed is described in U.S. Pat. No. 5,622,710. The granulation is accomplished in two steps. First, the fermentation broth is spray dried to produce particles of fermentation products and biomass. In the second step, the particles are converted into pellets by means of high shear mixing equipment. The additional step of using high shear mixing equipment to obtain a non-dusty product adds cost. Thus, there is a need for a process that leads to a non-dusty product which does not call for an expensive high shear mixing plant.

International Publication Number WO/95/23129 describes the production of non-stoichiometric salt of L-Lysine in granular form. This publication teaches the production of non-stoichiometric salts of L-Lysine wherein the amount of L-Lysine content in the final product is adjustable. While the requirement for hydrochloric acid is reduced, other materials are called for such as calcium hydroxide, sulfuric acid or phosphoric acid. In addition, the fermentation broth containing the L-Lysine is extensively ion-exchanged. Thus, there is a need for a more economical process to produce a granular product with an adjustable L-Lysine content which calls for fewer materials and which is not extensively ion exchanged.

U.S. Pat. No. 3,089,824 describes the use of a fluidized bed for the manufacture of compressed tablets for medical use. The process comprises (1) forming a suspension of particles in air, (2) enabling the particles to be built up with granulating material, and (3) coating the resulting granules with a lubricant. In one aspect of this invention, the granulating material is atomized and sprayed into the air stream of a fluidized bed of inert particles such as sucrose. The inert particles act as nuclei for the granulation process. The resulting granules are coated with a lubricant.

SUMMARY OF THE INVENTION

Accordingly, an object of this invention is to provide an improved process for producing a substantially dust free, free flowing granular L-Lysine from fermentation broth. A more particular object is to provide a simpler and more economical method for producing granular L-Lysine. In fact, an object is to produce a substantially dust free product that does not require a high shear mixing plant. A further object is to provide an L-Lysine product which is dried and granulated in one step, a process referred to here as an "agglomeration step".

Yet another object is to produce granular L-Lysine from a fermentation broth in which the concentration of L-Lysine is adjustable by adding L-Lysine freebase or L-Lysine monohydrochloride (hereafter referred to as "L-Lysine hydrochloride"). A more particular object is to avoid extensive ion exchange of the fermentation broth.

BRIEF DESCRIPTION OF THE DRAWING

The above mentioned and other feartures of this invention and the manner of obtaining them will become more apparent, and the invention itself will be best understood by reference to the following description of an embodiment of the invention taken in conjunction with the accompanying single sheet drawing, showing a flow chart depicting steps in the inventive process.

DETAILED DESCRIPTION OF PREFERRED EMBODIMENTS

While one aspect of this invention is the harvesting and processing of L-Lysine base from fermentation broth, the composition and nature of the fermentation medium may vary. For example, any suitable high L-Lysine producing organism taken from the genus Corynebacterium or Brevibacterium may be used to inoculate the fermentation medium. Prior to inoculation with the L-Lysine producing bacterium, the fermentation medium may have the following composition:

| Material | Amount (g/l) |
| --- | --- |
| Soy Hydrolysate | 20.0 |
| Ammonium Sulfate | 20.0 |
| Urea | 3.0 |
| Monopotassium Phosphate | 1.0 |
| Magnesium Sulfate heptahydrate | 0.5 |
| Manganese Sulfate | 0.002 |
| Biotin | 0.0001 |
| Thiamine Hydrochloride | 0.0001 |
| Glucose | 30.0 |

The pH is adjusted and maintained at 7.2 with ammonium hydroxide
The temperature is maintained at 32° C.
Feed consists of Glucose:$(NH_4)_2SO_4$; glucose concentration maintained at about 10g/l The fermentation medium can be inoculated into the fermentation vessel by using standard microbiological practices which are known to those with ordinary skills in microbiology. The fermentation vessel should be equipped with a stirrer, a ventilation system, and a temperature control device to maintain the fermentation at about 30° C. and preferably at 32° C. The fermentation is carried out until the L-Lysine base concentration is about 92 g/l (grams per liter) and the total dry solids is about 218 g/l. Aseptic techniques should be observed throughout the fermentation process to avoid a contamination of the fermentation broth with non-L-Lysine producing organisms.

In keeping with one aspect of this invention, which will be best understood with reference to the accompanying single sheet drawing, the process of producing the substantially dust free, free flowing, granular L-Lysine from fermentation broth might be described somewhat, as follows:

(i) An L-Lysine containing fermentation broth in fermenter 20 is ultrafiltered at 22 to remove cells in order to produce a substantially cell free L-Lysine permeate (show at 24 as "Permeate" on the attached figure). The retentate waste is drained off at 23. The ultrafilter used to remove the cells, has a molecular weight cutoff between about 10,000 Dalton and 500,000 Dalton, preferably about 500,000 Dalton.

(ii) The substantially cell free L-Lysine permeate is evaporated to remove water at 26 to produce a substantially cell free concentrated L-Lysine broth 28. Preferably, the substantially cell free concentrated L-Lysine broth 28 has between about 30% and 70% solids by weight. Waste water is drained away at 29. Evaporation is carried out in the approximate range of between 140° F. and 214° F., preferably between 145° F. and 155° F., and pressure between 2.9 psia and 11 psia (vacuum), preferably 2.9 psia to 4 psia.

(iii) The L-Lysine purity of the substantially cell free concentrated L-Lysine broth is adjusted to be in the range of about 35% and 76% L-Lysine, measured as a percent of freebase per kg. The adjustment is made by adding L-Lysine hydrochloride (shown as Lysine HCL in the attached figure) or L-Lysine freebase at 30 to provide a substantially cell free enriched L-Lysine broth in a mix tank 32.

(iv) The substantially cell free enriched L-Lysine broth is atomized by a nozzle 33 to provide an atomized spray of substantially cell free enriched L-Lysine broth to make a percolating bed of L-Lysine particulates in a spray granulator 34. The L-Lysine particulates have a particle size of less than about 177 micron (i.e. particles that can pass through 80 mesh) and preferably in the size range of about 100 micron and 177 micron. The bed of the spray granulator is preferably a fluidized bed of L-Lysine particulates and is operated at a temperature between about 30° C. and 100° C.

(v) The position of the nozzle 33 is adjusted until it is just above the fluidized bed of L-Lysine particulates.

(vi) Substantially cell free enriched L-Lysine broth is sprayed onto the fluidized bed of L-Lysine particulates to initiate the agglomeration process.

(vii) The agglomeration process is allowed to continue to produce the substantially dust free, free flowing, granular L-Lysine product in the size range between approximately 177 micron and 1190 micron, and preferably in the size range of between about 177 micron to 420 micron.

(viii) The product is removed from the spray granulator at 35, with waste water flowing away at 37 in the form of water vapor in the dryer exhaust.

(ix) The product is then screened and sorted for size at sieve 36 (preferably 80 mesh). This step is referred to as the "sieve step".

(x) Granules at 39 that are too large (e.g. in the size range of greater than about 1190 micron) are ground at 38 to a smaller particle size (e.g. in the size range of less than about 177 micron) and combined with material that is too small 41 (e.g. in the size range of less than about 177 micron) to produce recycled L-Lysine particulates (shown at 40 as "Recharge" on the attached figure) and returned to the spray granulator 34 as starting material to act as seeds for the agglomeration process.

(xi) The substantially dust free, free flowing, granular L-Lysine product in the size range of about 177 micron to 1190 micron (shown at 44 as "177–1190 micron Particles" on the attached figure) pass through the sieving process and are acceptable as the end product at 42. However, the preferred range is from about 177 micron to 420 micron since product in this size range packs better and reduces cost for shipment.

Although the preferred method for obtaining the substantially cell free L-Lysine broth is by means of ultrafiltration, this does not mean other methods can not be used. The cells could also be removed by mechanical separation techniques. For example, centrifugation can be used to obtain the substantially cell free L-Lysine broth.

The present invention also envisages the removal of cells from the L-Lysine containing fermentation broth by various processes. For example, the fermentation broth 20 could be split equally and about 50% centrifuged and the remaining 50% ultrafiltered and the outputs from both cell removal processes combined to produce a substantially cell free L-Lysine broth. It is envisaged that such flexibility will enhance the practice of the invention in an industrial setting.

Though the present invention envisages the addition of material containing L-Lysine to the substantially cell free concentrated L-Lysine broth at mix tank 32, the addition of material containing L-Lysine to the concentrated L-Lysine broth might be omitted altogether if the desired concentration of L-Lysine (measured as free-base) in the substantially cell free concentrated L-Lysine broth is such that the addition of material containing L-Lysine, as described above in step (iii), is unnecessary. For example, this step of adding either L-Lysine hydrochloride or L-Lysine free base might be omitted if the concentration of L-Lysine in the substantially cell free concentrated L-Lysine broth substantially exceeds about 35% L-Lysine, measured as a percent of freebase per kg. Should the cell free concentrated L-Lysine broth contain substantially more than about 35% L-Lysine, measured as a percent of freebase per kg, then the cell free concentrated L-Lysine broth may count as substantially cell free enriched L-Lysine broth.

Experience has shown that there is a relationship between the orifice size of the nozzle 33, flow rate, and gauge pressure. While the preferred nozzle size is 0.0615", various nozzles can be used to supply the spray. In particular, nozzle designs supplied by Spraying Systems Co., PO Box 7900, Wheaton, Ill. 60189-7900, USA (tel: 630-665-5000) work well to produce a fine spray. The spray granulator can be purchased from Glatt Air Techniques, 20 Spear Road, Ramsey, N.J. 07446-1288, USA (tel: 201-825-8700).

Experience also suggests that in order to manufacture L-Lysine granules on a commercial scale will require several nozzles to atomize and spray enriched L-Lysine broth onto a proportionally larger bed of percolating particles of L-Lysine.

The percolating bed of particles should comprise L-Lysine particles of sufficiently small size (e.g. <177 micron) to function as seeds for the agglomeration process. In the agglomeration process, the seed particles grow in size as they are sprayed with the enriched L-Lysine permeate. As the particles grow in size they also dry. Thus, the granulation and drying occurs simultaneously. The agglomeration process is aided by binders which are inherently present in the enriched L-Lysine broth, namely: L-Lysine fermentation broth, L-Lysine hydrochloride, L-Lysine freebase and water. A binder is defined as a substance which provides the sticky component to enable the seeds in the agglomeration process to build up in size.

The source of the L-Lysine particulates used to produce and seed the fluidized bed of L-Lysine particulates in the spray granulator is not critical although the preferred source is either obtained from atomizing the substantially cell free enriched L-Lysine broth as described in step (iv) above or from recycled L-Lysine particulates as described in step (x) above.

Alternatively, the fluidized bed of L-Lysine particulates could be produced by atomizing any of the following: L-Lysine containing fermentation broth from step (i), substantially cell free L-Lysine permeate from step (i), substantially cell free L-Lysine broth produced by centrifuging L-Lysine containing fermentation broth from step (i), substantially cell free concentrated L-Lysine broth from step (ii) or any combination of these.

In addition, purified L-Lysine hydrochloride and L-Lysine freebase could be used as a source for L-Lysine particulates in order to make the fluidized bed of L-Lysine particulates and to act as seeds for the agglomeration process. Also, the fluidized bed of L-Lysine particulates could be produced by spray drying to produce a powder of any of the following: L-Lysine containing fermentation broth from step (i), substantially cell free L-Lysine broth from step produced by centrifuging L-Lysine containing fermentation broth from step (i), substantially cell free L-Lysine permeate from step (i), substantially cell free concentrated L-Lysine broth from step (ii) or any combination of these. The resulting powder could be sieved and particles less than about 177 micron used as L-Lysine particulates.

While the exact source of the L-Lysine particulates for making the fluidized bed of L-Lysine particulates and the seeds for the agglomeration process is not too critical, it is preferable that the L-Lysine particulates are less than about 177 micron in size and preferably between about 100 micron and 177 micron.

In summary, suitable sources for making the L-Lysine particulates include: substantially cell free L-Lysine broth obtained from centrifuging L-Lysine containing fermentation broth from step (i), substantially cell free L-Lysine permeate from step (i), substantially cell free concentrated L-Lysine broth from step (ii), and substantially cell free enriched L-Lysine broth from step (iii). Each of these sources, or any combination of these sources, may be atomized by the nozzle 33 in the spray granulator 34 in order to generate the L-Lysine particulates. Alternatively, L-Lysine particulates may be made by separately spray drying, and possibly storing for later use, any of the following: substantially cell free L-Lysine broth obtained from centrifuging L-Lysine containing fermentation broth from step (i), substantially cell free L-Lysine permeate from step (i), substantially cell free concentrated L-Lysine broth from step (ii), and substantially cell free enriched L-Lysine broth from step (iii). Prior to use as L-Lysine particulates, the spray dried products may be sieved to remove lumps and to obtain particles in the size range of less than about 177 micron (preferably between about 100 micron and 177 micron). Excess water is drained away at 37.

For example the substantially cell free concentrated L-Lysine broth from step (ii) may be used to produce the bed of percolating bed of seed particles at 34. The substantially cell free concentrated L-Lysine broth may be atomized by the nozzle 33 in the spray granulator 34 in order to generate the percolating bed of seed particles. Alternatively, the substantially cell free concentrated L-Lysine broth may be separately spray dried. Prior to use as L-Lysine particulates, the spray dried concentrated L-Lysine broth may be sieved to remove lumps and to obtain particles in the size range of less than about 177 micron (preferably between about 100 micron and 177 micron).

Another example of a suitable source of the L-Lysine particulates would be dry purified L-Lysine hydrochloride powder which may be obtained by known state of the art processes. This dry powder may be used as a source for L-Lysine particulates or the dry powder may be sieved to remove lumps and sorted for particles less than about 177 micron (preferably in the size range between about 100 micron and 177 micron).

Experience has shown that once the agglomeration process becomes self-sustaining, the particles for the fluidized bed 34 comes from recycling particles at 40 into the into the fluidized spray granulator bed 34 by using particles at 41 which are too small or the granules which are too large and have been ground at 38 to a smaller size. Experience has also shown that the agglomeration process may operate on either a batch or semi-continuous basis. The batch process is preferred.

While the preferred L-lysine concentration in the starting feed stream, measured as a percent of freebase per kg, in the fermentation broth is about 90 g/l L-lysine, those skilled in the art will understand that L-lysine concentration can vary from one fermentation run to the next. Hence, the use of a fermentation broth containing about 90 g/l L-Lysine should not be taken to mean that other suitable concentrations of L-lysine in the fermentation broth are precluded. The final desired concentration of L-lysine may be achieved by adding L-Lysine hydrochloride (shown as Lysine HCL in the attached figure) or L-Lysine freebase at 30, and as described in step (iii) above. However, the L-Lysine concentration in the fermentation broth should not be below about 30 g/l.

The following examples represent specific but nonlimiting embodiments of the present invention:

EXAMPLE 1

Comparative Example 400 liters of fermentation broth with a L-Lysine concentration of 92 g/l (grams per liter) L-Lysine base and 218 g/l total dry solids were harvested from a L-Lysine fermentation run. This material was ultrafiltered and evaporated to a concentration of 235 g/l in the form of L-Lysine sulfate (measured as free base) and 493 g/l dry solids.

5150 ml (milliliters) of this concentrate was dried on a Glatt WSG 5 spray granulator. The inlet temperature of the Glatt unit was maintained between 93° C. and 124° C., preferably above 120° C. The outlet temperature was maintained between 40° C. and 80° C., preferably between 60 and 65° C. The bed temperature was maintained between 70 to 92° C., preferably between 71 and 74° C. The air flow was maintained between 1,300 and 4,000 feet per minute, preferably between 1,300 and 1,500 feet per minute. The nozzle atomization air was between 50 to 70 pound per square inch gauge. Approximately 2,500 ml of the concentrate was sprayed into the dryer with the nozzle in the highest setting in order to form a bed of material on which to agglomerate. The nozzle was lowered to a position just above the percolating material in the bed and agglomeration was accomplished with the remaining 2,650 ml of concentrate. This yielded a granulated product having the composition indicated in Table 1.

TABLE 1

| Sample | +16 mesh >1190 micron | +40 mesh 420 to 1190 micron | +80 mesh 177 to 420 micron | −80 mesh <177 micron | % Purity* |
|---|---|---|---|---|---|
| Broth | 16.1 | 58.3 | 25.5 | 0 | 46.5 |

*purity measured as percent L-Lysine freebase per kg

EXAMPLE 2

Lysine fermentation broth, ultrafiltered and concentrated as described above in Example 1, was mixed 4 to 1 (lysine basis) with purified L-Lysine sulfate (produced as a free base and pH adjusted to 6 with sulfuric acid yielding L-Lysine sulfate). The mixture was spray granulated as described in Example 1. The process is repeated with a 3 to 2 mixture, 2 to 3 mixture, 1 to 4 mixture and straight L-Lysine sulfate. The granulated products had the compositions as indicated in Table 2.

TABLE 2

| Sample | +16 mesh >1190 micron | +40 mesh 420 to 1190 micron | +80 mesh 177 to 420 micron | −80 mesh <177 micron | % Purity* |
|---|---|---|---|---|---|
| 4:1 | 11.6 | 50.9 | 26.1 | 11.4 | 49.0 |
| 3:2 | 28.1 | 17.1 | 49.1 | 5.7 | 52.2 |
| 2:3 | 0.9 | 40.3 | 52.5 | 6.3 | 57.4 |
| 1:4 | 6.1 | 35.0 | 41.8 | 17.1 | 62.5 |
| L-Lysine Freebase | 47.8 | 27.8 | 22.0 | 2.6 | 68.5 |

EXAMPLE 3

Lysine fermentation broth, ultrafiltered and concentrated as described above in Example 1, was mixed 4 to 1 (lysine basis) with pure L-Lysine hydrochloride was mixed 4 to 1 (lysine basis) with purified L-Lysine hydrochloride. The mixture was spray granulated as outlined in Example 1 above. The process was repeated with a 3 to 2 mixture, 2 to 3 mixture, 4 to 1 mixture and straight L-Lysine hydrochloride. The granulated products had the compositions as indicated in Table 3.

TABLE 3

| Sample | +16 mesh >1190 micron | +40 mesh 420 to 1190 micron | +80 mesh 177 to 420 micron | −80 mesh <177 micron | % Purity* |
|---|---|---|---|---|---|
| 4:1 | 7.4 | 33.0 | 59.6 | 0 | 49.4 |
| 3:2 | 7.6 | 32.9 | 44.2 | 15.2 | 51.5 |
| 2:3 | 4.8 | 48.4 | 46.8 | 0 | 57.0 |
| 1:4 | 5.1 | 45.3 | 49.4 | 0 | 66.6 |
| L-Lysine HCl | 17.2 | 44.5 | 29 | 9.3 | 76.8 |

It may be seen that mixing the concentrated and ultrafiltered L-Lysine fermentation broth of Example 1 with L-Lysine sulfate or L-Lysine hydrochloride, as described in examples 2 and 3 respectively, produces a granular product with increased L-Lysine content. It should also be apparent, to one with ordinary skills in the art, that one preferred embodiment of the described invention enables the L-Lysine content in L-Lysine fermentation broth to be easily adjusted prior to the agglomeration step. Thus, natural variations in L-Lysine concentration, which often occur from one L-Lysine fermentation to the next L-Lysine fermentation, do not require the extensive ion exchange to obtain a final product of the necessary purity for use (e.g. as a feed additive). The preferred level of purity in the final granular L-Lysine product being in the range between 35% and 76% L-Lysine, measured as a percent freebase per kg.

While the invention is described above in connection with preferred or illustrative embodiments, these embodiments are not intended to be exhaustive or limiting of the invention. Rather, the invention is intended to cover all alternatives, modifications and equivalents included within its spirit and scope of the invention, as defined by the appended claims.

What is claimed is:

1. A process for producing a substantially dust free, free flowing, granular L-Lysine comprising:
   (a) ultrafiltration of an L-Lysine containing fermentation broth to provide a substantially cell free L-Lysine permeate;
   (b) removing water from said substantially cell free L-Lysine permeate of step (a) to provide a substantially cell free concentrated L-Lysine broth;
   (c) adding a material containing L-Lysine to said concentrated substantially cell free L-Lysine broth of step (b) to provide a substantially cell free enriched L-Lysine broth; and
   (d) agglomerating the substantially cell free enriched L-Lysine broth of step (c) to provide a substantially dust free, free flowing, granular L-Lysine product.

2. The process of claim 1 wherein the ultrafiltration in step (a) to provide a substantially cell free L-Lysine permeate includes use of an ultrafilter having a molecular weight cutoff in the range between about 10,000 Dalton and 500,000 Dalton.

3. The process of claim 1 wherein the ultrafiltration in step (a) to provide a substantially cell free L-Lysine permeate includes use of an ultrafilter having a molecular weight cutoff of about 500,000 Dalton.

4. The process of claim 1 wherein step (b) comprises evaporating the L-Lysine permeate from said ultrafiltration step (a) to remove water in order to provide said substantially cell free concentrated L-Lysine broth.

5. The process of claim 4 wherein the evaporation of step (b) is carried out between about 140° F. and 214° F.

6. The process of claim 4 wherein the evaporation of step (b) is carried out between about 145° F and 155° F.

7. The process of claim 4 wherein the evaporation of step (b) is carried out in a vacuum between about 2.9 psia and 11 psia.

8. The process of claim 4 wherein the evaporation of step (b) is carried out in a vacuum between about 2.9 psia to 4 psia.

9. The process of claim 1 wherein the substantially cell free concentrated L-Lysine broth of step (b) has between about 30% and 70% solids by weight.

10. The process of claim 1 wherein said material containing L-Lysine of step (c) is selected from a group consisting of L-Lysine hydrochloride and L-Lysine freebase.

11. The process of claim 1 wherein the substantially cell free enriched L-Lysine broth of step (c) has between about 35% and 76% L-Lysine, measured as a percent of freebase per kg.

12. The process of claim 1 wherein the substantially cell free enriched L-Lysine broth of step (d) is agglomerated by using binders selected from a group consisting of L-Lysine fermentation broth, L-Lysine hydrochloride, L-Lysine freebase and water.

13. The process of claim 1 wherein the agglomeration process of step (d) comprises spraying the substantially cell free enriched L-Lysine broth onto a fluidized bed of L-Lysine particulates.

14. The process of claim 13 wherein said L-Lysine particulates are selected from a group consisting of recycled L-Lysine particulates, atomized substantially cell free L-Lysine broth, atomized substantially cell free L-Lysine permeate, atomized substantially cell free concentrated L-Lysine broth, atomized substantially cell free enriched L-Lysine broth, spray dried L-Lysine containing fermentation broth, spray dried substantially cell free L-Lysine broth, spray dried substantially cell free L-Lysine permeate, spray dried substantially cell free concentrated L-Lysine broth, and spray dried substantially cell free enriched L-Lysine broth, purified L-Lysine hydrochloride, and L-Lysine freebase.

15. The process of claim 13 wherein the L-Lysine particulates are in a size range of less than about 177 micron.

16. The process of claim 13 wherein the L-Lysine particulates are in a size range of between about 100 micron and 177 micron.

17. The process of claim 1 wherein step (d) comprises a step of passing the enriched L-Lysine broth through a nozzle to provide an atomized spray of substantially cell free enriched L-Lysine broth.

18. The process of claim 1 wherein the substantially dust free, free flowing, granular L-Lysine product of step (d) is in the size range between approximately 177 micron and 1190 micron.

19. The process of claim 1 wherein the substantially dust free, free flowing, granular L-Lysine product of step (d) is in the size range between approximately 177 micron and 420 micron.

20. A process for producing a substantially dust free, granular L-Lysine containing material comprising:
(a) removing cells from an L-Lysine containing fermentation broth to provide a substantially cell free L-Lysine broth;
(b) removing water from said L-Lysine broth of step (a) to provide a substantially cell free concentrated L-Lysine broth;
(c) adding a sufficient amount of material containing L-Lysine to said concentrated L-Lysine broth of step (b) to provide a substantially cell free enriched L-Lysine broth; and
(d) agglomerating the enriched L-Lysine broth of step (c) to provide a substantially dust free, free flowing, granular L-Lysine product.

21. The process of claim 20 wherein step (b) comprises a step of evaporating the L-Lysine broth of step (a) to remove water in order to provide said substantially cell free concentrated L-Lysine broth; said evaporation being carried out in a temperature range of about 140° F. and 214° F.; and said substantially cell free concentrated L-Lysine broth of step (b) is about 30% and 70% solids by weight.

22. The process of claim 21 wherein the temperature range is about 145° F. and 155° F.

23. The process of claim 21 wherein the evaporating step is carried out in a vacuum in a range of about 2.9 psia and 11 psia.

24. The process of claim 1 wherein the evaporating step is carried out in a vacuum between about 2.9 psia to 4 psia.

25. The process of claim 20 wherein said added material of step (c) is selected from a group consisting of L-Lysine hydrochloride and L-Lysine freebase, said added material being a quantity that brings the substantially cell free enriched L-Lysine broth of step (c) into a range of about 35% and 76% L-Lysine, measured as a percent of freebase per kg; and the enriched L-Lysine broth of step (d) is agglomerated by using at least one binder selected from a group consisting of L-Lysine fermentation broth, L-Lysine hydrochloride, and L-Lysine freebase and water which is mixed with and sprayed onto a fluidized bed of L-Lysine particulates, the particulates being selected from a group consisting of recycled L-Lysine particulates, atomized substantially cell free L-Lysine broth, atomized substantially cell free L-Lysine permeate, atomized substantially cell free concentrated L-Lysine broth, atomized substantially cell free enriched L-Lysine broth, spray dried L-Lysine containing fermentation broth, spray dried substantially cell free L-Lysine broth, spray dried substantially cell free L-Lysine permeate, spray dried substantially cell free concentrated L-Lysine broth, and spray dried substantially cell free enriched L-Lysine broth, purified L-Lysine hydrochloride, and L-Lysine freebase, said particulates being in the size range of less than about 177 micron.

26. The process of claim 25 wherein the L-Lysine particulates are in the size range of between about 100 micron and 177 micron.

27. A process for producing a substantially dust free, granular L-Lysine containing material comprising:
(a) removing cells from an L-Lysine containing fermentation broth to provide a substantially cell free L-Lysine broth;
(b) removing water from said substantially cell free L-Lysine broth by evaporating the substantially cell free L-Lysine broth in a temperature range of about 140° F. and 214° F. and in a vacuum out between about 2.9 psia and 11 psia to a concentration of L-Lysine which is between about 30% and 70% solids by weight to provide a substantially cell free concentrated L-Lysine broth;
(c) determining the concentration of L-Lysine, measured as a percent of freebase per kg, in the substantially cell free concentrated L-Lysine broth;

(d) adding a sufficient amount of material containing L-Lysine to said substantially cell free concentrated L-Lysine broth to provide a substantially cell free enriched L-Lysine broth if the concentration of L-Lysine in the concentrated L-Lysine broth, measured as a percent of freebase per kg, is below about 35%, said added material containing L-Lysine being selected from a group consisting of L-Lysine hydrochloride and L-Lysine freebase in a quantity which brings the L-Lysine into a range of about 35% and 76% L-Lysine, measured as a percent of freebase per kg; and (e) simultaneously drying and granulating the enriched L-Lysine broth to provide the substantially dust free, free flowing, granular L-Lysine containing product, the simultaneous drying and granulating of the substantially cell free enriched L-Lysine broth comprising the steps of spraying and atomizing the substantially cell free enriched L-Lysine broth onto a fluidized bed of L-Lysine particulates, the substantially cell free enriched L-Lysine broth being granulated by using binders selected from a group consisting of L-Lysine fermentation broth, L-Lysine hydrochloride, L-Lysine freebase and water.

* * * * *